United States Patent [19]

Fey et al.

[11] Patent Number: 5,273,877
[45] Date of Patent: *Dec. 28, 1993

[54] NON-HISTOLOGICAL CELL TYPE DETERMINATION

[75] Inventors: Edward G. Fey, Boston; Sheldon Penman, Brookline, both of Mass.

[73] Assignee: Massachusetts Institute of Technology, Cambridge, Mass.

[*] Notice: The portion of the term of this patent subsequent to Nov. 21, 2006 has been disclaimed.

[21] Appl. No.: 214,022

[22] Filed: Jun. 30, 1988

Related U.S. Application Data

[63] Continuation-in-part of Ser. No. 812,955, Dec. 24, 1985, Pat. No. 4,882,268, and Ser. No. 946,770, Dec. 23, 1986, Pat. No. 4,885,236.

[51] Int. Cl.$^5$ .................... C12Q 1/68; G01N 33/53; G01N 33/574
[52] U.S. Cl. .................... 435/6; 435/7.1; 435/7.2; 435/7.23; 435/820; 435/961; 436/501; 436/503; 436/63; 436/64; 436/813
[58] Field of Search .............. 435/6, 7, 29, 264, 268, 435/269, 270, 272, 7.1, 7.2, 7.23, 820, 961; 436/63, 64, 548, 501, 503; 530/350, 358, 387, 412, 420; 935/78; 536/27

[56] References Cited

U.S. PATENT DOCUMENTS 4,358,535 11/1982 Falkow ..................... 435/5
4,366,241 12/1982 Tom et al. ................. 435/5
4,569,916  2/1986 Penman .................... 436/64

OTHER PUBLICATIONS

Anderson et al., 30 (12) *Clin. Chem.* 1898-1905 (1984).
Barrack et al., 255 *J. Biol. Chem.* 7265-75 (1980).
Barrack et al, *Recent Progress in Hormone Research*, Roy O. Greep, (ed.) vol. 38, 133-137, and 180-189 (Academic Press, New York, 1982).
Berezney et al., 189(4199) *Science* 291-93 (1975).
Berezney et al., 14 *Adv. Enzyme Regul.* 63-100 (1976).
Berezney et al., 73 *J. Cell Biol.* 616-37 (1977).
Berezney et al., 85 *J. Cell Biol.* 641-50 (1980).
Bhorjee et al., 97 *J. Cell Biol.* 389-96 (1983).
Bludau et al., 165 *Exper. Cell Res.* 269-82 (1986).
Bodnar et al., 3 (9) *Mol. Cell Biol.* 1567-79 (1983).
Brasck et al., 54(2) *Biol. Cell* 109-21 (1985).
Briggs et al., 21 *J. Cellular Biochem.* 249-62 (1983).
Burdon et al., 825(1) *Biochim. Biophys. Acta.* 70-79 (1985).
Buttyan et al., 258(23) *J. Biol. Chem.* 14366-70 (1983).
Caizergues-Ferrer et al., 118(2) *Biochem. Biophys. Res. Com.* 440-50 (1984).
Capco et al., 29(3) *Cell* 847-58 (1982).
Chaly et al., 99 *J. Cell Biol.* 661-71 (1984).
Chaly et al., 63 *Can. J. Biochem. Cell Biol.* 644-53 (1985).
Chaly et al., 10(6) *Cell Biol. Inter. Reports* 421-28 (1986).
Chiu et al., 107 *Rad. Res.* 24-38 (1986).
Comings et al., 103 *Exp. Cell Res.* 341-60 (1976).
Detke et al., 257(7) *J. Biol. Chem.* 3905-11 (1982).
Eastment et al., 57(4) *Blood* 747-57 (1981).
Eisenman et al., 5(1) *Mol. Cell. Biol.* 114-26 (1985).
Fey et al., 98(6) *J. Cell Biol.* 1973-84 (1984).
Fey et al., 99 (1, Pt 2) *J. Cell Biol.* 203s-08s (1984).
Fey et al., 81(14) *Proc. Natl. Acad. Sci. USA* 4409-13 (1984).
Fey et al., 102 *J. Cell Biol.* 1654-65 (1986).
Fisher et al., 92(3) *J. Cell Biol.* 674-86 (1982).

(List continued on next page.)

*Primary Examiner*—Esther L. Kepplinger
*Assistant Examiner*—Toni R. Scheiner
*Attorney, Agent, or Firm*—Testa, Hurwitz and Thibeault

[57] ABSTRACT

Disclosed are non-histological methods for determining the presence in a sample of a preselected cell type such as a malignant or genetically defective cell, or cell nucleus debris from such cells. The methods involve determination of an intranuclear matrix protein, the mRNA encoding that protein, or matrix protein associated DNA or RNA which acts as a marker for the preselected cell type, the presence of which indicates the presence of the cell type in the test sample. The intranuclear matrix marker protein or nucleotide are detected by hybridization, immunoassay, or other known means.

22 Claims, 3 Drawing Sheets

OTHER PUBLICATIONS

Flickinger, 10(6) *Cell Biol. Internat. Reports* 415–20 (1986).
Franklin et al., 24 *J. Cell Biochem.* 1–14 (1984).
Hapbets et al., 54(1) *Clin. Exp. Immunol.* 265–76 (1983); 99(23) *Chem. Abstracts* No. 192945A (1983).
Hentzen et al., 81(2) *Proc. Natl. Acad. Sci. USA* 304–07 (1984).
Hodge et al., 72(1) *J. Cell Biol.* 194–208 (1977).
Intres et al., 21(11) *In Vitro Cell Dev. Biol.* 641–48 (1985).
Kaufman et al., 132 *Exp. Cell Res.* 105–23 (1981).
Kaufman et al., 155 *Exp. Cell Res.* 477–95 (1984).
Kirsch et al., 137(2) *Biochem. Biophys. Res. Comm.* 640–48 (1986).
Kuzmin et al., 25(20) *Eur. J. Cell. Biol.* 225–32 (1981).
Lehner et al., 162(1) *Exp. Cell Res.* 205–19 (1986).
Long et al., 18 *Cell* 1079–90 (1979).
Long et al, 48 *Biol. Cell* 99–108 (1983).
MacDonald et al., 138(1) *Biochem. Biophys. Res. Comm.* 254–60 (1986).
Martelli et al., 103(5, Pt. 2) *J. Cell Biol.* 181 (1986).
Milavetz et al., 134(2) *Virology* 406–20 (1984).
Milavetz et al., 127 *J. Cell. Physiol.* 358–96 (1986).
Moy et al., 46 *Cancer Res.* 4672–76 (1986).
Mullenders et al., 698 *Biochim. Biophys. Acta.* 70–77 (1982).
O'Farrell et al., 10 *J. Biol. Chem.* 4007–21 (1975).
O'Farrell et al., 82 *J. Cell Sci.* 173–86 (1986).
Prakash et al., 35 *Int. J. Cancer* 51–57 (1985).
Penman et al., 46(Pt 2) *Cold Spring Harbor Symp. Quant. Biol.* 1013–28 (1982).
Peters et al., 86 *J. Cell Biol.* 135–55 (1980).
Peters et al., 129 *Eur. J. Biochem.* 221–32 (1982).
Pienta et al., 1 *J. Cell Sci. Suppl.* 123–35 (1984).
Reiter et al., 76 *J. Cell Sci.* 17–33 (1985).
Schmidt et al., 44 *Cancer Res.* 5291–5304 (1984).
Shaper et al., 17 *Adv. Enzyme Regul.* 213–48 (1978).
Shelton et al., 255(22) *J. Biol. Chem.* 10978–83 (1980).
Simmen et al., 115(3) *Endocrinology* 1197–1202 (1984).
Simmen et al., 99(2) *J. Cell Biol.* 558–93 (1984).
Smith et al., 70 *Mol. Cell. Biochem* 151 14 68 (1986).
Song et al., 258(5) *J. Biol. Chem.* 3309 14 18 (1983).
Stastny et al., 30(12) *Clin. Chem.* 1914–18 (1984).
Staufenbiel et al., 31(2) *Eur. J. Cell Biol.* 341 14 48 (1983).
Staufenbiel et al., 98 *J. Cell Biol.* 1886–94 (1984).
Todorova et al., 783(1) *Biochim. Biophys. Acta.* 36–41 (1984).
Van der Velden et al., 782(4) *Biochim. Biophys. Acta.* 429–36 (1984).
Van Eekelen et al., 88 *J. Cell Biol. 554–63 (1981).*
Van Eekelen et al., 141 *Exp. Cell. Res.* 181–90 (1982).
Verheijen et al., 80 *J. Cell Sci.* 103–22 (1986).
Verheijen et al., 103 (5, Pt 2) *J. Cell Biol.* 179 (1986).
Werner et al., 151 *Exp. Cell Res.* 384–95 (1984).
Wojtkowiak et al., 42 *Cancer Res.* 4546–52 (1982).
Wu et al., 41 *Cancer Res.* 336–42 (1981).
Zbarskii et al., 1 *Macromol. Funct. Cell, Sov.-Ital. Symp., 2d* 114–23 (1982); 101(3) *Chem. Abstracts No. 192945A (1983).*
Fey, et al., 85 *Proc. Natl. Acad. Sci. USA* 121–25 (1988).

LUNG

ADRENAL CORTEX

BLADDER

COLON

NON-HISTOLOGICAL CELL TYPE DETERMINATION

BACKGROUND OF THE INVENTION

The U.S. Government has certain rights in this invention by virtue of National Institute of Health Grant Numbers 5RO1 CA08416-20 and 1RO1 CA37330-01 and National Science Foundation Grant Number PCM 8309334.

REFERENCE TO RELATED APPLICATIONS

This application is a continuation-in-part of U.S. application Ser. No. 812,955, filed Dec. 24, 1985, now U.S. Pat. No. 4,882,268, entitled "Method for Determining Tissue of Origin and Degree of Malignancy of Tumor Cells" and of application Ser. No. 946,770, filed Dec. 23, 1986, now U.S. Pat. No. 4,885,236 entitled "Method for Determining Tissue of Origin and Presence and Extent of Cellular Abnormalities". The disclosures of each of these co-pending applications is herein incorporated by reference. Related subject matter is disclosed in published international application Ser. No. WO87/03910.

This invention relates to a non-histological method of determining cell type, and more particularly to a method of detecting the presence of a given cell type, or debris from a cell type, in a sample such as a blood sample, exfoliated cell sample, fine needle aspirant cell sample, biopsied tissue sample or sample containing cell debris, which obviates or diminishes the need to examine the morphology of a tissue sample or individual cells thereof.

Diagnosis of viral infection, cancer, chromosomal defects or autoimmune disease is often difficult and inexact. Heretofore, determining the presence of tumor cells or other abnormal cells in a tissue sample has been the province of the clinical pathologist, and is generally based on observation of the morphology of the cells or tissue in histological preparations. Such diagnosis has serious limitations and cannot always distinguish tumor type and tissue of origin. There is a great need for alternative means of identifying cell type and stage of malignancy or abnormality. Chromosomal defects can be detected only in the case of gross morphological defects or where the proteins encoded by the missing or defective genes are known and can be assayed for. Viral infections can usually be diagnosed only by measuring antibody levels, examination of cells, and presence of clinical symptoms.

There is also a need for a means of identifying the site of tissue damage, not only in autoimmune diseases where the target cell is known, but also, for example, in bladder infection or myocardial infarction, where cell degradation products are released into the urine or bloodstream.

Attempts have been made to determine cell type by analysis of the protein composition of whole cell extracts. However, these extracts contain a number of different proteins, of which the vast majority do not vary among cell types. Even with techniques providing increased resolution between proteins, such as the more recent methods of two dimensional gel electrophoresis, such efforts have largely failed to find meaningful differences in proteins that can reliably serve as a basis for cell and tissue type identification. Even where there might be a change in proteins due to infection or malignancy, existing methods fail to differentiate the new or altered proteins from background proteins.

All eucaryotic cells, both plant and animal, have a nucleus surrounded by the cell cytoplasm. The nucleus contains the cellular DNA complexed with protein and termed chromatin. The chromatin, with its associated proteins, constitutes the major portion of the nuclear mass. The chromatin is organized by the internal protein skeleton of the nucleus, referred to here as the intranuclear matrix.

The prior art contains many reports of attempts to investigate the nature of "nuclear matrix proteins" in various cell types. Generally, the reports involve attempts to isolate such proteins from various types of cells, and often to compare proteins from different cell types. However, the reported nuclear matrix protein isolation techniques result in poorly defined preparations including not only the intranuclear matrix proteins, but also the relatively insoluble nuclear membrane laminae and pore proteins, intermediate filaments and chromatin protein components. Although it has been hypothesized that such preparations contain cell-type specific proteins, the prior art fails to provide reliable methods of separating specific non-chromatin intranuclear matrix proteins from the much larger quantity of chromatin proteins and intermediate filaments. The methods that have been used either separated out the soluble proteins and discarded the insoluble proteins, or used high salt (2M NaCl) and other harsh reagents to extract these nuclear matrix proteins.

There has been limited success in biochemically identifying cells by analyzing the protein composition of the intermediate filaments. The intermediate filaments are proteins present in the cytoplasm of all cells which have been discovered to be anchored to the nucleus, and to be useful to discriminate between five major classes of cells: epithelial, neuronal, glial, muscle and mesenchymal cells such as fibroblasts. Labeled antibodies to these proteins only serve to distinguish among these broad cell classes, although some further discrimination is possible with epithelial cells.

In the above-referenced copending applications, methods are disclosed for isolating the intranuclear matrix proteins, i.e., proteins from within the boundaries of the nuclear matrix, termed "interior" nuclear matrix proteins, which are substantially free of chromatin proteins and intermediate filaments, collectively termed "exterior" nuclear matrix proteins. In the method, the cell nucleus is isolated, the cytoskeleton proteins and chromatin are removed, the "nuclear matrix" isolated, and the "interior" and "exterior" components of the nuclear matrix are separated. The nuclear matrix-intermediate filament complex comprises a specific fraction of cell protein constituting less than five percent of the total protein and six percent of the total DNA of the cell. The intranuclear matrix comprise about one percent or less of the total cellular protein. It contains many proteins that differ according to cell type, and is highly enriched with cell type-specific antigens including cell-type and transformation-specific proteins that have not been detected using prior art procedures. It also contains the lamina and nuclear pore complex proteins which do not significantly differ with cell type. The separation method makes use of the unique properties of the intranuclear matrix to achieve separation from substantially all other cell constituents. The method is simple, rapid, reproducible, achieves a high degree of purity, is applicable to essentially all types of cells.

SUMMARY OF THE INVENTION

It has been discovered that individual cell types comprise intranuclear matrix proteins or combinations of proteins which are unique to the cell type. It is hypothesized that intranuclear matrix proteins play a role in determining which portion of the genome of a cell is expressed in a particular cell type. Since the genome of all somatic cells of a particular individual are nearly identical, cell type is dictated by differences in gene expression. Thus, it is possible to identify a cell type by assaying for intranuclear matrix proteins which act as markers identifying the cell type. The term "cell type" as used herein, refers to cells of various different tissues such as neural, glial, muscle, mesenchymal, different types of epithelia, and endothelia, as well as malignant cell forms and cells having an altered genomic expression profile caused by viral infection or other factors.

The foregoing observation, made possible by the discovery of methods for isolating intranuclear matrix proteins, has permitted the development of a generalized method of detecting a preselected mammalian cell type (hereinafter "cell type") in a cell sample or sample containing cell nucleus debris. The method comprises the step of detecting the presence in the sample of an intranuclear matrix protein known to be associated with the cell type. The cell type may be, for example, a malignant cell, detected, for example, in an exfoliated sample such as a cervical cell sample, a fine needle aspirant sample, a blood sample, a biopsied sample, or a sample containing cell debris including the matrix proteins. In accordance with the invention, either an individual intranuclear matrix protein "unique" to the cell type, a plurality of separate intranuclear matrix proteins having a relative abundance "unique" to the cell type, or relative quantities of proteins may be assayed as a means of identifying the cell type.

The methods employed for detecting the protein or proteins generically are well known to the art. For example, one or more monoclonal antibodies or polyclonal antisera specific to intranuclear matrix proteins may be suitably labeled and employed as a probe to detect the presence of the marker proteins in a suitably prepared cell sample. Alternatively, labeled polynucleotides may be used in conventional DNA/DNA, RNA/DNA, or RNA/RNA hybridizations to detect the polynucleotides associated with the intranuclear matrix proteins, i.e., physically mixed with the intranuclear matrix and/or which encode the intranuclear matrix marker protein. Preferably, useful antibodies or polynucleotides are labeled with a substance detectable by optical methods such as flourescent dyes. However, enzymatic labels, colloidal sized colored particles, radioactive atoms, and other known labeling agents may be used.

Practice of the invention enables production of a large number of assays, each of which is designed to detect the presence of a given cell type in a sample, limited only by the availability of authentic samples obtainable from repositories, laboratories, and biopsy. To design such assays, the intranuclear matrix proteins from a plurality of authentic samples of cells is isolated using, for example, the techniques disclosed herein and in the above-referenced copending applications. At least one of the proteins is selected to serve as a marker for the preselected cell type. That is, the selected marker protein, if present in the sample, identifies the sample as containing a cell, or being derived from tissue containing a cell, of the preselected cell type. It is not required that the selected protein be totally unique, in the sense that the particular intranuclear matrix protein is present in the target cell type and in no other. Rather, it is required that the intranuclear matrix protein marker have a signal to noise ratio high enough to discriminate the preselected cell type in samples for which the assay is designed. For example, a marker protein indicating the presence of malignancy in exfoliated human cervical cell samples would be useful even though the particular intranuclear matrix protein selected as a marker, or a close analog thereof, were present commonly in a particular type of cell from a different species or in human samples from a separate tissue. Marker proteins can be identified with confidence by examining a representative number of tissue samples known to be normal and cell type positive samples, and then selecting the intranuclear matrix protein marker or markers to achieve an adequate level of discrimination, i.e., an adequate signal.

Next, an assay for the marker protein or proteins is prepared using known techniques. Monoclonal antibodies or polyclonal antisera, suitably labeled, may be used to advantage. Also, it is within the scope of the invention to construct labeled nucleotide probes to detect the presence of "unique" RNA or DNA associated with the intranuclear matrix protein. In preferred embodiments, labels are used to facilitate detection of the protein in situ so that after suitable sample preparation, involving membrane breakdown or membrane permeabilization, and preferably removal of soluble protein components, the presence of the protein can be detected directly on the sample.

Accordingly, it is an object of the invention to provide non-histological methods for determining the presence of malignant cells, virally infected cells, genetically defective cells, or other abnormal cell types in cell samples. Another object is to provide methods of determining the tissue of origin of cells or cellular debris shed into body fluids.

These and other objects and features of the invention will be apparent from the description and claims which follow.

Figure 1A:
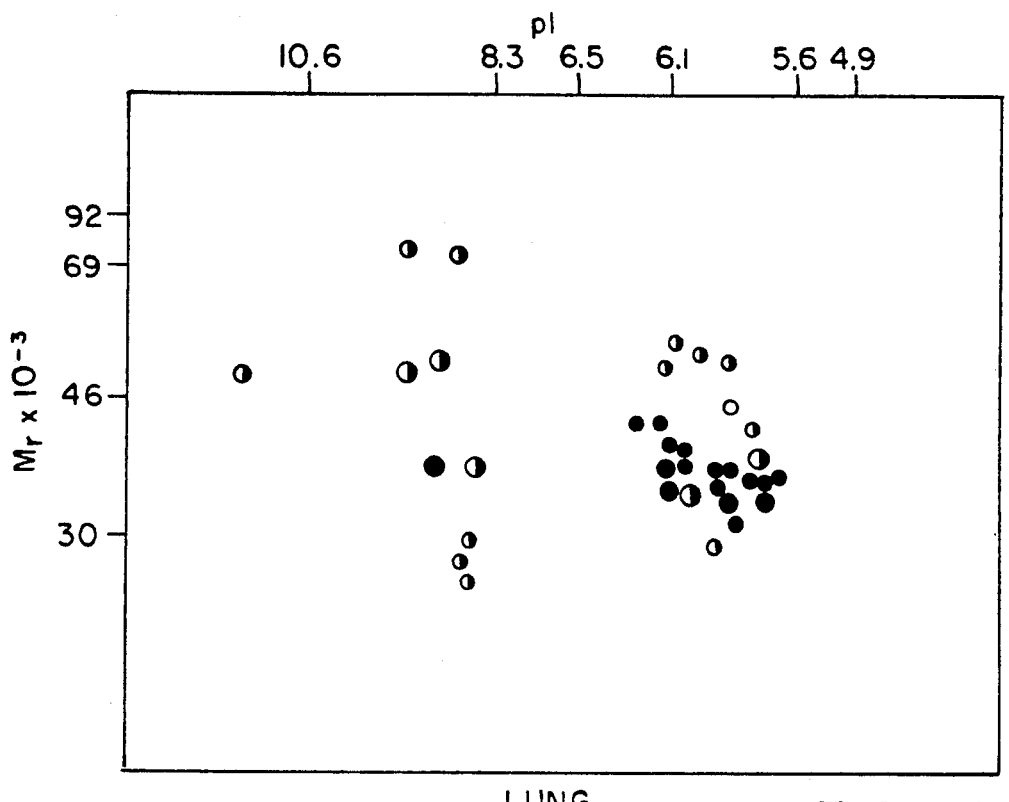
FIGS. 1(A and B) is a comparison of diagramatic two-dimensional electropherograms (PI v. m.w.) of nuclear matrix proteins from FIG. 1A, a human lung tumor cell line (black circles) and FIG. 1B, an adrenal cortex tumor cell line (white circles, adenocarcinoma) where proteins common to both are shown as half black circles.
Figure 1B:
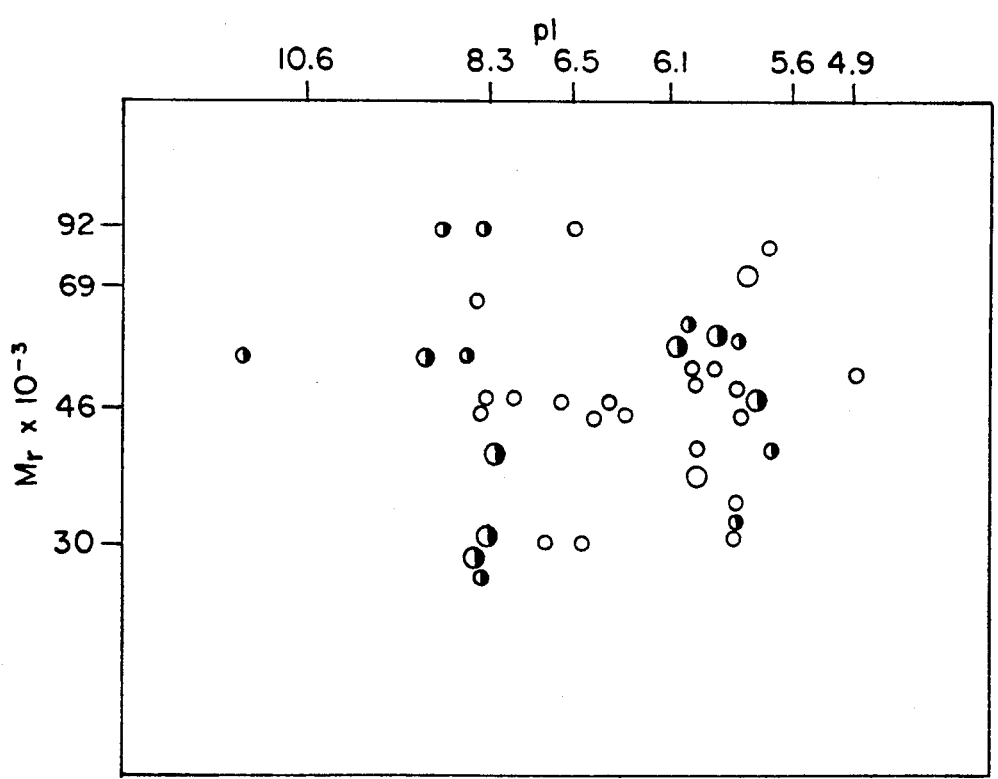
Figure 2B:
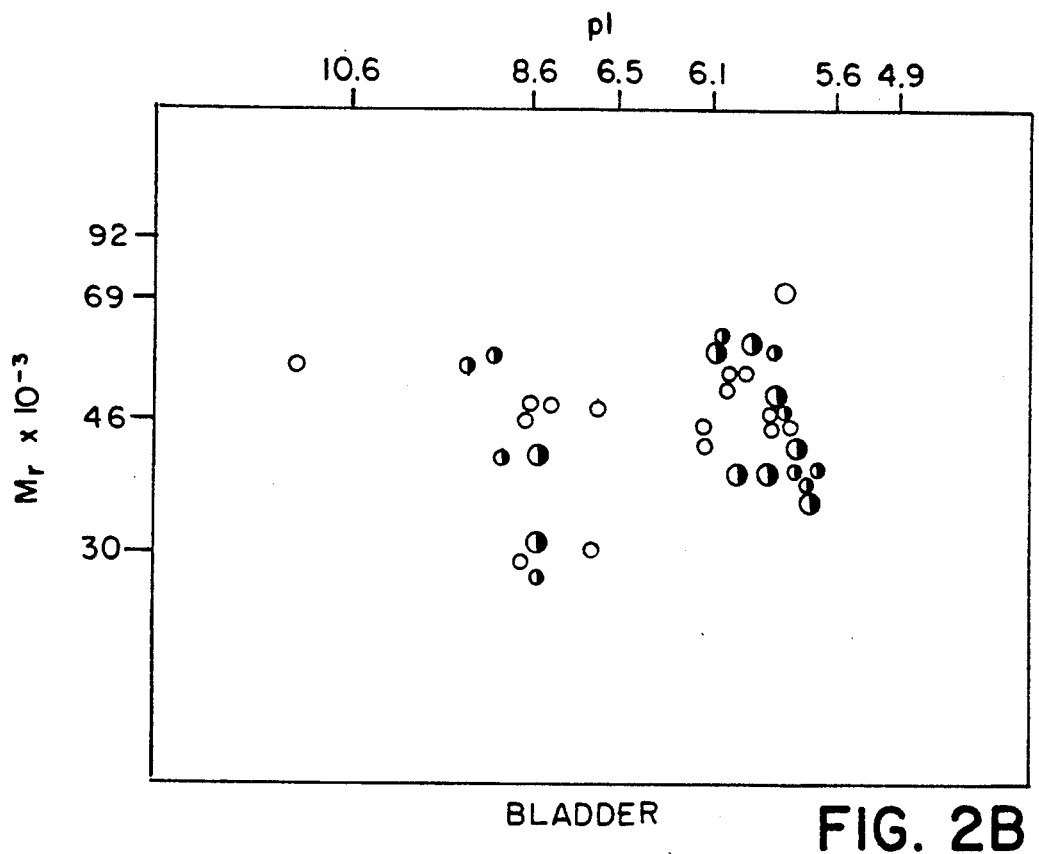
FIGS. 2(A and B) is a comparison of diagramatic two-dimensional electropherograms (PI v. m.w.) of intranuclear matrix proteins from FIG. 2A a human colon tumor (black circles) and FIG. 2B, bladder tumor (white circles), where proteins common to both are shown as half black circles.
Figure 2A:
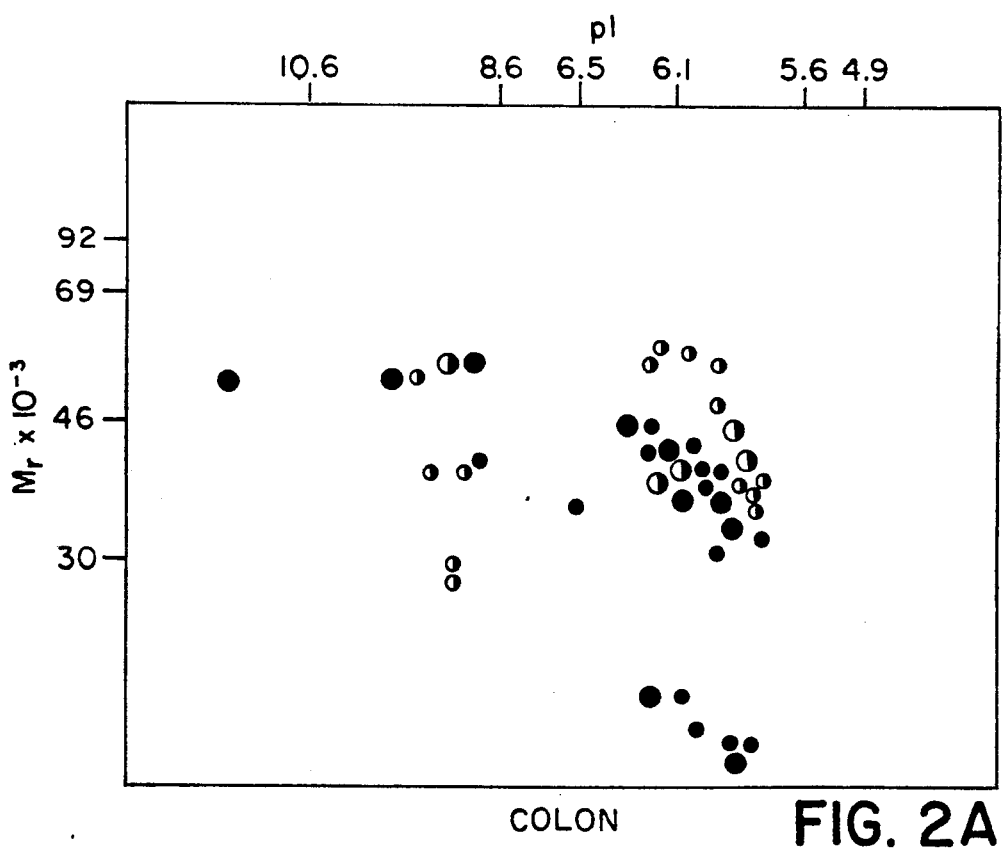

m.w.) of intranuclear matrix proteins from a cervical carcinoma with a squamous morphology (ATCC CCL 1594) and a cervical carcinoma with a basal cell morphology (ATCC HTB33).

DESCRIPTION

In the description which follows, the generalized method for isolating and identifying intranuclear matrix proteins and associated DNA which act as markers to specific cell types are disclosed. This involves isolation of the intranuclear matrix proteins, their separation, and visual or biological screening procedures useful in selecting marker materials. Next, methods are disclosed for designing assays useful for detecting the marker proteins.

The nuclear matrix is purified from a cell suspension prepared from a tissue biopsy or blood sample, separated into its "interior" and "exterior" fractions, and then analyzed by two-dimensional gel electrophoresis. Prior to the development of this technique, it is believed that no one had been able to separate the intranuclear matrix proteins in a way which did not cause extensive degradation or contamination with large amounts of extraneous protein. The nuclear matrix protein complex broadly accounts for less than approximately five percent of the total cell protein. The "interior" proteins, or intranuclear matrix together with nuclear pore proteins and lamina, represent less than one percent of the total protein, with the "exterior" or "intermediate filament" and chromatin proteins making up the remainder. The intranuclear matrix proteins reflect the structure and composition of the cell being examined. The lamina and pore proteins often do not differ with cell type. The exterior matrix proteins, by virtue of containing the intermediate filaments, reflect the class of the cell being examined (neuronal, epithelial, etc.). By separating the exterior proteins from the intranuclear matrix proteins, the sensitivity and specificity with which the intranuclear matrix proteins can be identified is greatly enhanced since the exterior matrix proteins comprise a major amount of the total protein of the fraction and their presence can obscure less abundant but important marker proteins.

Broadly, the isolation procedure involves the following:

1. Isolation and separation of cells.
2. Separation of soluble cell proteins from the nucleus and cytoskeleton by extraction of membrane lipids and soluble proteins with a non-ionic detergent-physiological salt solution.
3. Separation of cytoskeleton proteins from the nucleus by solubilization of the insoluble cell material from step 2 in either 0.25M ammonium sulfate, pH 6.8, a detergent-sodium deoxycholate solution, or other gentle extraction buffer.
4. Separation of chromatin from the nuclear matrix by digestion of the insoluble material from step 3 with DNAase I and RNAase in a physiological buffer and elution of the DNA-containing nucleosomes with 0.25M ammonium sulfate solution buffered to pH 6.8 or other gentle extraction buffer.
5. Separation of the intranuclear and "exterior" nuclear matrix proteins by dissolution of the insoluble material from step 4 in a buffer containing between 5 and 10M urea, preferably 8M urea, or other suitable solubilizing agent, and aggregation of the exterior proteins by dialysis into physiological buffer.

Further purification of the intranuclear proteins can be performed using HPLC, FPLC, chromatofocusing, and other methods known to those skilled in the art.

In a variation of this procedure, the cytoskeleton proteins and chromatin are removed together by digesting the insoluble material from step 2 with DNAase and RNAase, then extracting with 0.25M ammonium sulfate at pH 6.8.

In another variation, the nuclear matrix associated DNA is isolated and analyzed, alone or in conjunction with the intranuclear matrix proteins. The method consists of treating the insoluble material from step 2 with DNAase then 0.25M ammonium sulfate at physiological pH to remove the chromatin. A phenol extraction and/or centrifugation in $CsCl_2$ is then performed to remove any remaining protein. In a variation of this method, the insoluble material from step 2 is digested with a restriction enzyme in the appropriate buffer, the chromatin extracted with 0.25M ammonium sulfate pH 6.8, then any remaining protein removed by phenol extraction and/or centrifugation in $CsCl_2$.

More specifically, the isolation procedure involves the following steps.

Cell Preparation

The procedure employs single cells of the preselected cell type sought to be detected in a suspension. Cells in blood samples or from cell culture may be treated directly. Tissues obtained by biopsy are dispersed by mild mechanical homogenization followed by digestion with a proteolytic enzyme such as collagenase or trypsin. These enzymes digest connective fibers between cells without affecting the interior contents. In cases where it is desirable to perform an initial, partial separation of cell types, a rapid cell separation is effected by centrifugation, an inert density gradient, or by other known means for rapidly separating cells without chemical interaction.

Purification of the Nuclear Matrix Proteins and Associated DNA

The nuclear matrix is separated from other cell constituents by a series of sequential extractions. The cell suspension is exposed to the extraction solution for one to two minutes and then the insoluble material separated by centrifugation (approximately one to two minutes at 1000 g), filtration (pore size approximately 5 microns), or other method known to those skilled in the art. One key feature of this extraction process is that harsh extractants such as 2M NaCl or organic reagents are avoided. A second is the use at an appropriate stage of urea or other suitable solubilizing agent to dissolve the intranuclear and exterior proteins, followed by repolymerization and ultimate separation of the exterior proteins. The steps are as follows:

1. Removal of soluble cell proteins.

The soluble proteins, amounting to 70% of the cell mass, are removed by extracting the intact cell with a non-ionic detergent solution, such as 0.5% Triton X-100. The non-ionic detergent in a buffer at physiological pH and ionic strength extracts first the membrane lipids and then the soluble proteins. The detergent solubilizes lipids without denaturing proteins and thus avoids disturbing the integrity of the cell structures. The physiological salt solution is essential to maintain the morphology of the cytostructure and to prevent the removal of structural elements. An example of a useful buffer is 100 mM NaCl, 300 mM sucrose, 10 mM PIPES [pH 6.8], 3 mM $MgCl_2$, 0.5% Triton X-100, 1.2 phenylmethylsulfonylfluoride at 4° C.

2. Removal of cytoskeleton proteins.

The cytoskeleton proteins are next separated from the nucleus by selective solubilization of the cytoskeleton proteins amounting to 20% of cell protein mass, with either a 0.25M ammonium sulfate solution buffered to pH 6.8, for example, 0.25M ammonium sulfate, 0.3M sucrose, 10 mM PIPES [pH 6.8], phenylmethylsulfonyl fluoride, 0.5% Triton X-100, or with a 1% Tween-40, 0.5% sodium deoxycholate solution. The nucleus, with all of the intermediate filaments still attached, and including the cromatin, amounting to about 10% of the total cellular proteins, remains.

3. Removal of the chromatin proteins

The chromatin proteins, whose association with the nucleus depends on the integrity of DNA and RNA, is next separated from the nuclear matrix. The nucleus is first digested with DNAase and RNAase in near physiological digestion buffer, for example, 50 mM NaCl, 0.3M sucrose, 10 mM PIPES [pH 6.8], 3 mM $MgCl_2$, 0.5% Triton X-100, 1.2 mM phenylmethylsulfonyl fluoride with 100 micrograms bovine pancreatic DNAase (EC 3.1.4.5, Worthington Biochemical Corp., Freehold, N.J.) and 100 micrograms/ml pancreatic RNAase A (EC 3.1.4.22., Sigma Chemical Co., St. Louis, Mo.). The enzyme cuts DNA between the nucleosomes. At this stage, the DNA remains completely in the nucleus in the form of individual nucleosomes. The DNA-containing nucleosomes are then eluted for approximately 5 minutes at 20° C. using 0.25M ammonium sulfate buffered to pH 6.8. Although 0.25M ammonium sulfate is preferred, comparable buffers could be used.

4. Separation of the Intranuclear and Exterior Proteins of the Matrix

The nuclear matrix, consists of less than 5% of the cell protein mass, is further divided into two distinct parts, termed herein the intranuclear and exterior. The exterior part consists of the intermediate filaments and intermediate filament associated proteins such as the nuclear pore proteins and lamina separate with the intranuclear matrix. Although the filaments are exterior to the matrix, in the cytoplasm, they are physically connected to the nuclear matrix. They and their associated proteins amount to greater than one-half of the proteins in the matrix preparation.

Fractions selectively enriched in the intranuclear and exterior matrix proteins are produced by completely dissolving the matrix proteins in a buffered 5 to 10M urea solution, preferably 8M, or other suitable solubilizing agent such as, for example, lithium di iodosalicylate, as required to completely dissolve all nuclear matrix proteins, and then dialyzing the proteins in physiological buffer. The intranuclear proteins remain in solution. The intermediate filament proteins and associated proteins reassemble into large insoluble filaments during dialysis to remove the solubilizing agent. The urea or comparable solubilizing agent is essential for dissolving the proteins, which are generally quite insoluble. Removal of the solubilizing agent, as by dialysis, is essential to reform the intermediate filament fractions, thereby permitting their separation.

In a variation of the method, the cytoskeleton proteins and chromatin are removed together. The soluble proteins are first removed by extraction with a non-ionic detergent buffered solution. The insoluble material is digested with DNAase and RNAase in a buffered solution. Then the cytoskeleton proteins and chromatin extracted with 0.25M ammonium sulfate at physiological pH.

The selectively enriched intranuclear matrix protein fraction can be further separated by electrophoresis, "chromatofocusing" (BioRad Laboratories, Richmond, Calif.), HPLC and related technologies such as FPLC (fast protein liquid chromatography), isoelectrofocusing, and conventional ion exchange or affinity chromatography.

The highly purified intranuclear matrix proteins may be analyzed using conventional two-dimensional acrylamide gel electrophoresis. Typical results are illustrated in the drawings. The proteins are first separated in a pH gradient gel according to electrophoretic mobility or isoelectric point. This gel is then placed on a standard 10% acrylamide slab gel and the proteins separated according to molecular weight. One method of two dimensional gel electrophoresis is taught by P. H. O'Farrell in *J. Biol. Chem.* 250, 4007–4021 (1975) using an ampholyte gradient consisting of 90% pH 5–7 (0.4% ampholyte) and 10% pH 3–10 (1.6% ampholyte). The proteins from a pattern of spots, made detectable by silver staining or by autoradiography, comprise individual proteins or subsets of proteins which are diagnostic of the cell type or state of transformation or abnormalities.

Immunoblot electrophoresis can also be used to identify relevant proteins in the intranuclear matrix. The procedure for immunoblot electrophoresis is as follows. One-dimensional polyacrylamide gels are run according to the method of Laemmli in *Nature* (Lond.), 227,680–685 (1970). Equal protein concentrations are loaded to compare individual fractions. The reaction of antibodies to protein bands are visualized after electroelution on nitrocellulose paper according to the procedure of H. Towbin et al., *Proc. Natl. Acad. Sci. USA*, 76,4350–4354 (1979). Nitrocellulose strips are incubated for 12 hours in 2% hemoglobin in PBS, rinsed three times in PBS, and incubated for 2 hours at 20° C. with antibody to the protein to be detected at the appropriate concentration. Excess antibody is removed by washing with PBS (four 20 minute washes). The strips are then incubated with goat anti-rabbit (or anti-mouse) IgG conjugated to horseradish peroxidase, washed in PBS (four times for a total of 80 minutes) and then developed in 0.4 mg/ml 4-chloro-1-naphthol in 0.01% (vol/vol) $H_2O_2$ using the technique of R. Hawkes et al., in *Anal. Biochem.*, 119,142–147 (1982).

The matrix preparation is biochemically and morphologically pure by several biochemical criteria. It retains most matrix specific constituents. Freedom from contamination permits a clear and detailed analysis of the matrix proteins by gel electrophoresis. Individual matrix proteins useful as cell-type discriminators often comprise less than 0.01% of the cell's total protein.

Cell type specificity of intranuclear matrix proteins has been demonstrated using cultured cell lines and human cell samples. These include common laboratory lines such as primary and established fibroblasts, HeLa cells, etc. Perhaps most relevant to clinical applications are the results from a number of carcinoma lines derived from human biopsy and exfoliated normal and malignant cervical cell samples. As shown in the drawings these include human colon, lung, cervical, adrenal cortex, and bladder cells. The electropherogram patterns are markedly different in different cell types, but each cell type contains unique as well as common proteins (including lamin and nuclear pore). The pattern for each cell type is specific and reproducible. Similar results can be obtained with animal tissue.

Analysis of the nuclear matrix associated DNA and RNA provides redundant or additional information for determining the cell type, tissue of origin, and degree of abnormality of cells. "Actively" transcribed DNA in a cell is usually associated with the nuclear matrix proteins. This DNA represents approximately 6% of the total cell DNA. Different quantities of DNA as well as specific sequences of DNA will be associated with the nuclear matrix and nuclear matrix proteins, depending on cell type and whether the cell is abnormal and to what degree the cell is abnormal.

Generally, markers comprising protein, its mRNA, or matrix associated DNA can be used to:

1. Identify general cell type (e.g., epithelial, neuronal, etc.).
2. Identify specific cell type (e.g., colon epithelium, breast epithelium, etc.). This allows identification of the origin of metastasis or site of cell damage.
3. Determine the nature and degree of malignancy, genetic deficiency, defect, or disease.
4. Identify cells or cell fragments shed into body fluids including cerebro spinal fluid, urine, serum, semen, sputum, peritoneal fluid, and feces where the presence of the cell or fragment indicates a diseased state.

Screening Procedures

From the foregoing it should be apparent that the intranuclear matrix proteins comprise a reservoir of proteins and nucleic acids that may be used as markers to identify cell types. In order to achieve the objects of the invention, it is necessary to screen for a protein, group of proteins, polynucleotide, or group of polynucleotides that will be useful as a marker to enable cytological, non-histological determination of cell type in a cell sample. Broadly, the selection procedure involves screening a number of known positive cell samples and a number of negative samples to permit identification of a common intranuclear matrix protein or nucleotide marker in the positive samples not present in the negatives. Screening may be conducted by isolating the intranuclear matrix protein as disclosed above, separating the proteins, preferably using two-dimensional gel electrophoresis, and then manually, electronically, or biochemically examining the gel patterns to locate a protein positioned on the gels produced from the positive samples but absent from the negative samples.

In the screening procedure, the nature of the sample to be analyzed may be taken into account to simplify the task. For example, if a marker for malignant cells in exfoliated cervical cell samples is desired, the marker protein should be present in all cervical malignant cells and absent from non-malignant cervical cell samples, but the fact that the marker protein or a close analog thereof may be present in other types of human cells not found in cervical tissue samples is immaterial. Stated differently, a marker for a malignant cell will not induce false positives if the same marker protein is present in an unrelated tissue.

The two dimensional gels suggest proteins useful as markers in that, as disclosed in the drawings, they clearly show proteins present in a first cell type which are absent from a second cell type.

The proteins selected as markers may be isolated by gel slicing or elution onto nitrocellulose or another substrate. Antibodies raised against marker proteins may be produced using well known and established methods based on the seminal Kohler and Milstein paper (Nature, 256:495-497, 1975). For example, spleen cells from a mouse immunized against the isolated marker protein are fused with an appropriate murine myeloma cell line, e.g., P3X63-Au8.653. The mouse is immunized by several injections of the protein over a period of several weeks. When the mouse shows sufficient antibody titre against the complex, as determined by conventional assay methods, it is given a booster injection of the complex, sacrificed, and its spleen removed. The fusion is then initiated utilizing spleen cells from immunized mice and an appropriate myeloma cell line (e.g., P3X63-Au8.653). The hybridomas yielding antibodies specific for the immunogenic complex are selected in a standard hypoxanthine, aminopterin, and thymidine (HAT) medium and cloned utilizing standard methods. The monoclonal antibodies from the clones are then tested to determine their specificity for the particular marker protein.

Additional useful procedures for isolating marker proteins disclosed below are designed to locate proteins which not only serve as markers, but also are antigenically distinct and therefore capable of positive identification by immunoassay. In order to insure the generation of monoclonal antibodies to diagnostic proteins, several antigen preparations and several distinct immunization procedures may be employed. These measures are desirable to insure an immunoresponse from low abundance proteins and to mask any immunodominant proteins that are present in the matrix preparations. These procedures are preferred over techniques involving recovery of proteins from 2D gels, as such recovered proteins may comprise epitopes in common with irrelevant proteins, thereby decreasing their utility as markers identifiable using monoclonal antibodies.

Figure 4A:
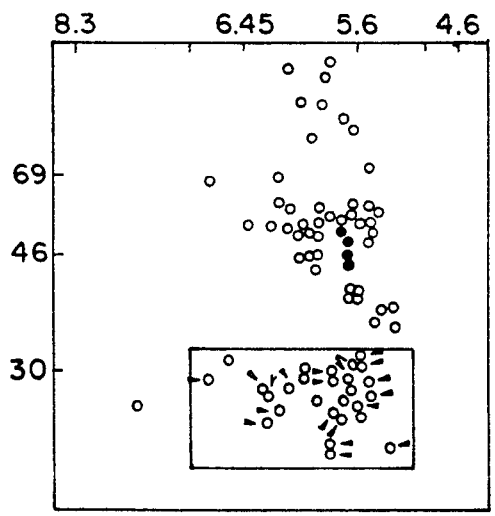
FIGS. 4a and 4b show is a comparison of diagramatic, two-dimensional electropherograms (PI v.

Using tumor antigen purified from established cervical carcinoma cell lines (for example, HTB33, FIG. 4b, and CCL 1594, FIG. 4a, available from the American Type Culture Collection) and normal antigen from primary cervical keratinocytes Stanley et al. *Growth Requirements of Human Cervical Epithelial Cells in Culture*, Int. J. Cancer 24, 407-414, 1979), monoclonal antibodies can be generated that differentiate between normal and cancerous cells of the cervix for use as cytochemical and histochemical reagents. In one successful technique, Balb/c mice were immunized at two week intervals by intraperitoneal injection with 250 to 500 ug of nuclear matrix protein in an adjuvant containing monophosphoryl lipid A and trehalose dimycolate (Ribi). The fifth injection was done without adjuvant, and spleens were removed for fusion four days later. Splenocytes were fused with myeloma cells of the P3X63 AG8.653 line in 50% (w/v) PEG 1500 (polyethylene glucol) in 75 mM HEPES, pH 8.01, for 1 minute at 37° C., before selection in HAT containing medium. Hybridomas were grown in RPMI-1640 containing 15 mM HEPES, pH 7.4, and 10% (v/v) hybridoma tested fetal bovine serum. When cells were plated at low density, as in subcloning by limiting dilution, 50 ug/ml endothelial cell growth supplement (Collaborative Research) was included. Antibody is produced either by harvesting culture medium or from ascites fluid after injection of the cells into pristane primed Balb/c mice.

Figure 3A:
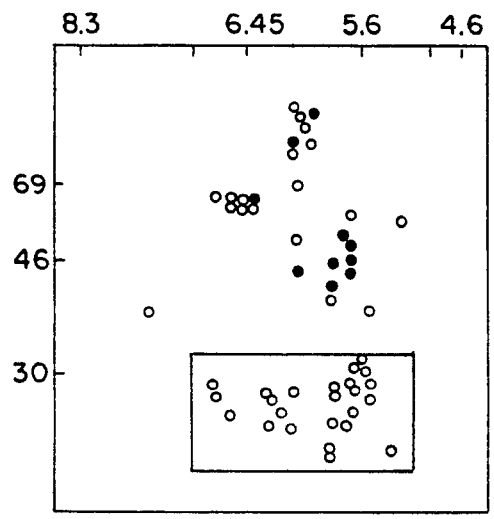
FIGS. 3a and 3b show is a comparison of diagramatic, composite, two-dimensional electropherograms (PI v. m.w.) of intranuclear matrix proteins from a plurality of known normal exfoliated cervical cell samples and a plurality of exfoliated cervical cell samples known to contain carcinoma.
Figure 3B:
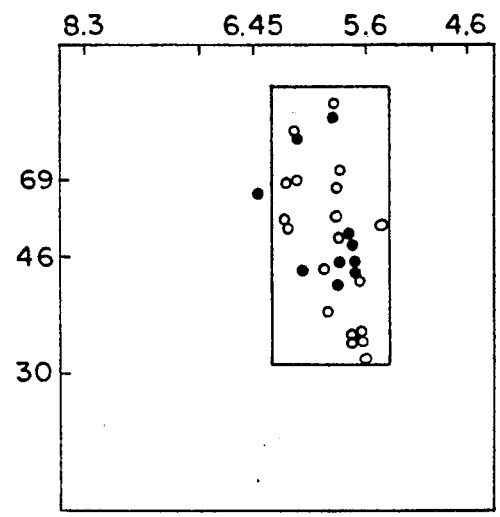
Figure 4B:
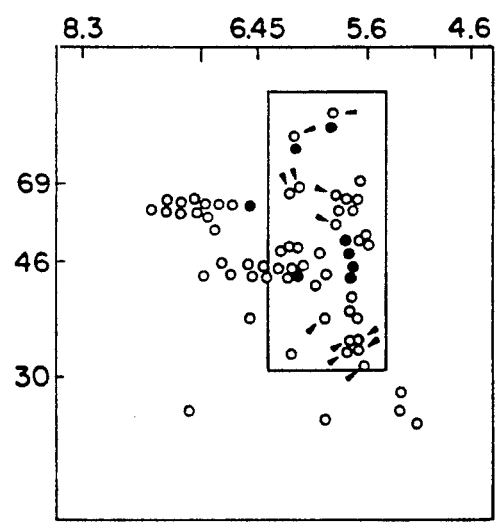

In initial fusions, regions (shown in Boxes, FIG. 4a and 4b) rich in potentially antigenic diagnostic proteins (see arrows) indicating "normal" nuclear matrix proteins (FIG. 4a) from the CCL1594, a corresponding fraction from cultured keratinocytes, or a similar fraction from cultured "normal" cervical cells (Box FIG. 3a), in the molecular weight range <30KD (pI 4.8-6.0), can be purified using gel filtration and chromatofocusing and may be used as a source of purified normal proteins. Nuclear matrix protein from HTB33 in the molecular weight range >30KD, (pI 4.8-6.4, Box in FIG. 4b) may be used as a source of purified tumor marker proteins. Note the common proteins in the boxes of FIGS. 3b and 4b. Those marked with arrows in FIG. 4b are present in the matrix protein from FIG. 3b but not in FIG. 3a (the normal cells) or in FIG. 4a (the model of normal squamous cells). These fusions can provide antibodies to the abundant, diagnostic proteins observed in the cervical smears (Boxes FIGS. 3a and 3b) for differentiating normal and malignant samples. Specific monoclonal antibodies or panels of antibodies with binding properties suitable for commercial scale assay of cervical smears can be selected from the fusions using standard screening techniques of authentic normal and malignant cervical cell samples as disclosed below.

In another approach, total nuclear matrix protein from primary (normal) keratinocytes and known cervical carcinoma cell lines are used to make antibodies. This 'shotgun' fusion permits the production of monoclonal antibodies to diagnostic antigens not resolved in the two-dimensional gels due to sensitivity limitations in that technique. The fusion products may be screened in duplicate using, for example, ELISA employing multiple plates containing both normal and tumor cell antigen, for those antibodies capable of differentiating normal from malignant cells.

A third approach is based on the cyclophosphamide method described by Matthew and Sandrock (Matthew et al, *Cyclophosphamide Treatment Used to Manipulate the Immune Response for the Production of Monoclonal Antibodies*, J. Immun. Meth. 100, 73-82, 1987). In this procedure, the presence of immunodominant antigens is suppressed. Mice immunized with nuclear matrix protein antigen from normal cells are treated with cyclophosphamide to destroy the proliferating B cells. The mice are then immunized with antigen from tumor cell nuclear matrix. The resulting monoclonals made from conventional spleen fusions are enriched in antibodies elicited to matrix proteins present in the preparation from the malignant cell intranuclear matrix which were not generated in response to the first immunization. Thus, these antibodies distinguish the malignant antigens from the normal antigens. This procedure enables production of antibodies to weakly immunogenic proteins, in effect using the mouse immune system as a discriminator. In both these latter screening approaches, antibodies useful in the process of the invention may be identified without ever locating or isolating the marker protein they recognize.

The fusion products may be screened further using conventional ELISA microtitre techniques as noted above. (See, e.g., Wood, *Solid-phase screening of monoclonal antibodies*. 1984, in: J. M. Walker (ed.), *Proteins*, 279-286. Humana Press, Clifton, N.J.). Coated microtitre plates are prepared with the "normal" nuclear matrix fractions and the "abnormal" nuclear matrix fraction. Antibodies that show differential binding to these coated wells are sub-cloned to ensure the monoclonal nature of the cells, prepared in larger quantities, and screened against fixed tissue sections of cervical carcinoma and normal cervix. The immunohistochemical screening can be performed using conjugated antimouse immunoglobin antibodies. (See, for example, Fey et al, *Epithelial Cytoskeletal Framework and Nuclear Matrix-Intermediate Filament Scaffold: Three-dimensional Organization and Protein Composition*, J. Cell Biol., 98, 1984, 1973-1984). Those antibodies showing the ability to differentiate between carcinoma and normal tissue can then be produced in larger quantities for development of test formats for subsequent immunocytochemical studies and clinical trials on exfoliated cervical cell samples.

While the foregoing is disclosed with reference to identifying markers for differentiating normal from malignant cervical cell samples, it will be appreciated that the procedures can be used to develop assays for many other cell types.

When these monoclonal antibodies (or polyclonal antisera) to marker proteins are conjugated with colorimetric, immunological (such as labeled anti-antibody), fluorescent, enzymatic or radioactive labels, they can be used as cytological stains on histological sections or for analysis of body fluids or protein preparations separated by two dimensional gel electrophoresis to provide useful diagnostic information. The antibodies can detect the presence of tumor or viral antigens, abnormal proteins or the absence thereof due, for example, to a defective chromosome or genetic deficiency, and proteins released during cell destruction, as in some types of infection, myocardial infarction, necrosis, and autoimmune diseases.

Intranuclear matrix associated DNA and RNA can be analyzed and identified using gel electrophoresis and blot hybridization with probes specific for a particular unique sequence or repetitive sequence. Probes may be made by inserting the sequence of interest, either a synthetic sequence or a portion of the gene of interest, into a recombinant plasmid using methods known to those skilled in the art. The probes can be conjugated with a radiolabel, biotinylated, or crosslinked with psoralin and derivatives thereof for use as a double stranded probe. Such probes can be used in assays, imaging, isolation and identification procedures.

More specifically, gene probes comprising complementary RNA or, preferably, DNA to the nuclear matrix associated nucleotide sequences or mRNA sequences encoding nuclear matrix proteins may be produced using established recombinant techniques or oligonucleotide synthesis. The probes hybridize with complementary nucleic acid sequences presented in the test specimen, and can provide exquisite specificity. A short, well-defined probe, coding for a single unique sequence is most precise and preferred. Larger probes are generally less specific. Choices of probe length and sequence allows one to choose the degree of specificity desired. Hybridization is carried out at from 50° to 65° C. in a high salt buffer solution, formamid or other agents to set the degree of complementarity required. The state of the art is such that probes can be manufactured to recognize essentially any unique DNA or RNA sequence. For further particulars, see, for example, *Guide to Molecular Techniques*, Berger et al, Methods of Enzymology, Vol. 152, 1987.

Labeling Technology

A wide variety of different labels may be employed coupled to the probes or antibodies for use in assays. The label reagents may be provided in solution or coupled to a insoluble support, depending on the design of the assay. The various conjugates may be joined covalently or noncovalently, directly or indirectly. When bonded covalently, the particular linkage group will depend upon the nature of the two moieties to be bonded in their respective functions. A large number of linking groups and methods for linking are taught in the literature. Broadly, the labels may be divided into the following categories: chromogens; catalyzed reactions; chemiluminescence; radioactive labels; and colloidal-sized colored particles. The chromogens include compounds which absorb light in a distinctive range so that a color may be observed, or emit light when irradiated with light of a particular wavelength or wavelength range, e.g., fluorescers. Both enzymatic and nonenzymatic catalysts may be employed. In choosing an enzyme, there will be many considerations in addition to those involved with a reaction of interest, including the stability of the enzyme, whether it is normally present in samples of the type for which the assay is designed, the nature of the substrate, and the effect if any of conjugation on the enzyme's properties. Potential useful enzyme labels include oxiodoreductases, transferases, hydrolases, lyases, isomerases, ligases, or synthetases. Interrelated enzymes systems may also be used. A chemiluminescent label involves a compound which becomes electronically excited by a chemical reaction and may then emit light which serves as a detectable signal or donates energy to a fluorescent acceptor. Radioactive labels include various radioisotopes found in common use such as the unstable forms of hydrogen, iodine, phosphorous or the like. Colloidal size colored particles involve material such as colloidal gold which, in aggregation, form a visually detectable distinctive spot corresponding to the site of the substance to be detected. Additional information on labeling technology is disclosed, for example, in U.S. Pat. No. 4,366,241, the disclosure of which is incorporated herein by reference.

The most common method of in vitro labeling of nucleotide probes involves nick translation wherein the unlabeled DNA probe is nicked with an endonuclease to produce free 3' hydroxyl termini within either strand of the double-stranded fragment. Simultaneously, an exonuclease removes the nucleotide residue from the 5' phosphoryl side of the nick. The sequence of replacement nucleotides is determined by the sequence of the opposite strand of the duplex. Thus, if labeled nucleotides are supplied, DNA polymerase will fill in the nick with the labeled nucleotides. Using this well known technique, up to 50% of the molecule can be labeled. For smaller probes, known methods involving 3' end labeling may be used. Furthermore, there are currently commercially available methods of labeling DNA with fluorescent molecules, catalysts, enzymes, or chemiluminescent materials. Biotin labeling kits are commercially available (Enzo Biochem, Inc.) under the trademark Bio-Probe. This type of system permits the probe to be coupled to avidin which in turn is labeled with a fluorescent molecule, enzyme, antibody, etc.

For further disclosure regarding probe construction and technology, see, for example Maniatis et al, *Molecular Cloning, A Laboratory Manual* (Cold Springs Harbor, N.Y., 1982); and Wahl et al, PNAS (Wash), 76, 3683-3687, 1979.

Assay Design

Many specific protocols for detecting the presence of nuclear matrix marker proteins in cell samples or samples containing cell debris are available and known to those skilled in the art. Generally, the optimal procedure will depend on the nature of the desired assay and the preference of the designer. Broadly, assays may be designed which are intended for the determination of a particular cell type in a fixed cell sample, on the one hand, or for detecting the presence of a particular marker protein in a fluid such as cerebrospinal fluid, blood, serum, urine, etc., as an indication of the presence of the cell type, or debris from the cell type, in the fluid. The literature contains a large volume of disclosure on methods and rationals for designing immunoassays and nucleic acid hybridization assays which are general in scope and can easily be adapted to detect the intranuclear matrix marker proteins and related nucleic acids located in accordance with the procedures disclosed herein.

Hybridization technology may be used which includes dot blot hybridization, in situ hybridization, sandwich hybridization, affinity labeling, and solution analysis. In dot blot hybridization, radioactively tagged probes are used to visualize the sequence of interest by autoradiography. The in situ approach involves preparation of a section or smear which is incubated with the probe, washed, and then visualized by autoradiography. Sandwich hybridization involves a procedure similar to the dot blot technique, but a homologous fragment is included which anneals to a membrane and the probe. Affinity labeling refers to the insertion of nucleotides into the probe which are labeled with fluorescent materials or enzymes. In solution analysis, crude samples are mixed with the probe, nuclease inhibitors, lysing agents, and reagents which promote hybridization, and the products are separated and imaged by autoradiography.

For assays based on the use of monoclonal antibodies, broadly, the procedures include in situ immunological staining, and various methods for assaying for the presence of a particular ligand (an intranuclear matrix protein) in a liquid sample. For a disclosure of the construction of monoclonal antibody based assays, see, for example, U.S. Pat. No. 4,376,110 entitled "Immunometric Assays Using Monoclonal Antibodies" issued to David et al, the disclosure of which is incorporated herein by reference. The currently preferred assay protocol involves a sandwich or competitive assay using monoclonal antibodies in a test cartridge of the type wherein the immunological reactions take place in a porous membrane, and reagents are drawn through the membrane by means of an absorbent material disposed therebeneath. This type of device and assay protocols are disclosed in the U.S. Pat. No. 3,888,629, the disclosure of which is incorporated herein by reference.

In the assays conducted in accordance with the invention, regardless of the particular selected protocol, it is often advantageous to pretreat the sample so as to remove soluble proteins, i.e., proteins from the cytoplasm, cell surface proteins, etc., so as to increase the relative amount of nuclear matrix protein present in the sample. This can be done, for example, using the first two steps of the intranuclear matrix isolation technique disclosed above. This can significantly increase the signal to noise ratio and improve sensitivity and specificity of the assay. In any case, it is necessary to disrupt cell membranes or render them permeable so that the diagnostic reagents employed in the assay can reach the nuclear matrix to react.

Analysis of either the proteins, mRNA encoding those protein or the DNA provides a means to determine the presence of chromosomal defects or genetic deficiencies which might otherwise be undetectable. One application is in the analysis of cells obtained by amniocentesis. Another is in the identification and assessment of autoimmune diseases. Both the antibodies and hybridization probes can be used to analyze cellular materials and body fluids, both in vivo (tissue imaging) and in vitro, for nuclear matrix proteins. As noted above, steps to concentrate or enhance the antigen levels in the body fluids often are desirable to increase the signal ratio. Once probes or antibodies are developed, for example, to carcinoma specific proteins, they can be labeled and used to rapidly screen cell samples such as a smear or a body fluid.

The rapid, analytical procedures of the present invention provide a means for an objective determination of the tissue of origin of normal and abnormal cells and their degradation products, thereby indicating whether transformation or infection of normal cells has occurred, whether there has been metastasis and to what degree, and whether the individual has an autoimmune disease. The procedure dispenses with the need to examine cell morphology in assessing cell type, or limits the instances where such observations are necessary.

Although the invention has been described with reference to specific embodiments, variations and modifications of the method for diagnosing cells of unknown tissue type or state of malignancy, infection or abnormality will be apparent to those skilled in the art. It is intended that such modifications and variations fall within the scope of the appended claims.

What is claimed is:

1. A method of detecting a preselected mammalian cell type in a sample containing cells or cell nucleus debris, the method comprising the steps of:
   a) contacting said sample with a specific binding partner which specifically binds an intranuclear matrix protein known to be present in said preselected cell type, and
   b) detecting the presence in the sample of said intranuclear matrix protein.

2. The method of claim 1 wherein said preselected cell type is a malignant cell.

3. The method of claim 1 wherein the detecting step is conducted by detecting the presence of an antibody bound to said matrix protein.

4. A method of detecting a preselected mammalian cell type in a sample containing cells or cell nucleus debris, the method comprising the steps of:
   a) contacting said sample, under hybridization conditions, with a labelled nucleotide probe which specifically hybridizes with an intranuclear matrix protein-associated marker polynucleotide known to be present in said preselected cell type, and
   b) detecting the presence in said sample of said marker polynucleotide.

5. The method of claim 4 wherein said preselected cell type is a malignant cell.

6. The method of claim 1 wherein a plurality of separate intranuclear matrix proteins are detected, the presence of which indicates the presence of said preselected cell type in said sample.

7. The method of claim 1 wherein a plurality of separate intranuclear matrix proteins are detected, the relative abundance of which indicates the presence of said preselected cell type in said sample.

8. The method of claim 1 wherein a relative quantity of an intranuclear matrix protein present in the sample is detected, the abundance of which indicates the presence of said preselected cell type in said sample.

9. The method of claim 1 wherein the sample is an exfoliated cell sample.

10. The method of claim 1 wherein the sample is a fine needle aspirant cell sample.

11. The method of claim 1 wherein the sample is a blood sample.

12. The method of claim 1 wherein the sample is a biopsied cell sample.

13. The method of claim 3 wherein the antibody is labeled with a substance detectable by an optical method.

14. The method of claim 5 wherein the labeled polynucleotide is labeled with a substance detectable by an optical method.

15. The method of claim 1 comprising the step of removing detergent soluble proteins from the sample prior to said detecting step.

16. A method of detecting a preselected mammalian cell type in a sample containing cells or cell nucleus debris, the method comprising the steps of:
   a) isolating intranuclear matrix proteins from a plurality of authentic samples of cells of said preselected cell type;
   b) selecting at least one of said intranuclear matrix proteins to serve as a marker protein for said preselected cell type, the presence of which in a sample identifies the sample as containing a cell of said preselected cell type or cell nucleus debris therefrom;
   c) preparing a specific binding partner which specifically binds said marker protein in a said sample;
   d) contacting said sample with said specific binding partner; and
   e) detecting the presence of said marker protein in said sample, the presence of said marker protein indicating the presence in said sample of said preselected cell type or cell nuclear debris therefrom.

17. The method of claim 16 wherein step (b) further comprises selecting a plurality of the proteins of step (a) to serve as marker proteins, the presence or relative abundance of which in a sample identifies the sample as containing a cell of said preselected cell type or the cell nucleus debris therefrom, step (c) further comprises preparing a specific binding partner for each of said plurality of proteins in said sample, step (d) further comprises contacting said sample with said specific binding partners, and step (e) further comprises detecting the presence in said sample of said plurality of marker proteins or the relative abundance thereof.

18. The method of claim 1 wherein said sample comprises a body fluid.

19. The method of claim 18 wherein said body fluid is selected from the group consisting of cerebro-spinal fluid, urine, serum, semen, sputum, peritoneal fluid and feces.

20. The method of claim 4 wherein said sample comprises a body fluid.

21. The method of claim 20 wherein said body fluid is selected from the group consisting of cerebro-spinal fluid, urine, serum, semen, sputum, peritoneal fluid and feces.

22. The method of claim 16 wherein said a specific bonding partner is an antibody.

* * * * *

UNITED STATES PATENT AND TRADEMARK OFFICE
CERTIFICATE OF CORRECTION

PATENT NO. : 5,273,877
DATED : Dec. 28, 1993
INVENTOR(S) : Fey et al.

It is certified that error appears in the above-indentified patent and that said Letters Patent is hereby corrected as shown below:

On the title page, item [75] Inventors: should read:
[75] Inventors: Sheldon Penman, Brookline; Edward G. Fey, Boston, both of Mass.

Signed and Sealed this

Seventeenth Day of May, 1994

Attest:

BRUCE LEHMAN

*Attesting Officer*     *Commissioner of Patents and Trademarks*